(12) United States Patent
Roberts et al.

(10) Patent No.: US 6,756,223 B2
(45) Date of Patent: Jun. 29, 2004

(54) ELECTRO-CHEMICAL ANALYSIS DEVICE WITH INTEGRATED THERMAL SENSOR AND METHOD FOR MONITORING A SAMPLE USING THE DEVICE

(75) Inventors: Peter C. Roberts, Gilbert, AZ (US); Frederic Zenhausern, Fountain Hills, AZ (US); Jeremy W. Burdon, Scottsdale, AZ (US); Daniel J. Sadler, Gilbert, AZ (US)

(73) Assignee: Motorola, Inc., Schaumburg, IL (US)

( * ) Notice: Subject to any disclaimer, the term of this patent is extended or adjusted under 35 U.S.C. 154(b) by 393 days.

(21) Appl. No.: 10/024,704

(22) Filed: Dec. 18, 2001

(65) Prior Publication Data

US 2003/0113907 A1 Jun. 19, 2003

(51) Int. Cl.⁷ ............................................. C12M 1/34
(52) U.S. Cl. ............................. 435/287.2; 435/288.3; 435/91.2; 422/98; 422/109; 204/403.03; 204/403.13
(58) Field of Search .................... 435/287.2, 288.3, 435/288.7, 91.2; 422/98, 109; 204/403.03, 403.13

(56) References Cited

U.S. PATENT DOCUMENTS

| | | |
|---|---|---|
| 5,945,286 A | 8/1999 | Krihak et al. |
| 5,981,166 A | 11/1999 | Mandecki |
| 6,013,170 A | 1/2000 | Meade |
| 6,013,446 A | 1/2000 | Maracas et al. |
| 6,013,459 A | 1/2000 | Meade |
| 6,048,699 A | 4/2000 | Foley et al. |
| 6,063,573 A | 5/2000 | Kayyem |
| 6,071,699 A | 6/2000 | Meade et al. |
| 6,080,969 A | 6/2000 | Goto et al. |
| 6,083,762 A | 7/2000 | Papen et al. |
| 6,087,100 A | 7/2000 | Meade et al. |
| 6,090,933 A | 7/2000 | Kayyem et al. |
| 6,096,273 A | 8/2000 | Kayyem et al. |

(List continued on next page.)

FOREIGN PATENT DOCUMENTS

| | | |
|---|---|---|
| EP | 1108472 A2 | 6/2001 |
| EP | 1120646 A1 | 8/2001 |
| WO | WO97/18226 | 5/1997 |
| WO | WO 01/02094 A1 | 1/2001 |
| WO | WO 02/086162 A1 | 10/2002 |
| WO | WO 02/090963 A1 | 11/2002 |

OTHER PUBLICATIONS

Eisen, M.B. et al., Proc. Natl. Acad. Sci., 95, p. 14863–8, (1998).
Spellman, P.T., et al., Molecular Biology of the Cell, 9, p. 3273–97, (1998).

(List continued on next page.)

Primary Examiner—David A. Redding
(74) Attorney, Agent, or Firm—William E. Koch

(57) ABSTRACT

An electro-chemical analysis device and method for analyzing biomolecular samples, including a means for holding a sample on a substrate platform, a thermal sensor, a biosensor formed having a specific spatial resolution as related to the thermal sensor, and a means for providing radiation to the biomolecular sample. The means for holding the sample, the thermal sensor, the biosensor, and the means for providing radiation all three-dimensionally integrated with the substrate platform, thereby defining a compact biomolecular analysis device having a volume resolution of less than 50 micro liters. During operation, radiation is provided to the biomolecular sample to provide for a constant temperature at which hybridization of the biomolecules takes place. The temperature of the biomolecular sample is monitored and controlled by the integrated thermal sensor and the integrated heater. Once hybridization takes place, the change in electric condition (e.g. voltage, current and/or power) is recorded and identification of the molecule within biomolecular sample is made by utilizing an exterior reader.

18 Claims, 2 Drawing Sheets

U.S. PATENT DOCUMENTS

| | | |
|---|---|---|
| 6,230,497 B1 | 5/2001 | Morris et al. |
| 6,261,782 B1 | 7/2001 | Lizardi et al. |
| 6,264,825 B1 | 7/2001 | Blackburn et al. |
| 6,266,459 B1 | 7/2001 | Walt et al. |
| 6,277,576 B1 | 8/2001 | Meade et al. |
| 6,285,490 B1 | 9/2001 | Meier et al. |
| 6,290,839 B1 | 9/2001 | Kayyem et al. |
| 6,309,833 B1 | 10/2001 | Edman et al. |
| 6,312,960 B1 | 11/2001 | Balch et al. |

OTHER PUBLICATIONS

Brazma, A., et al., Genome Research, 8, p. 1202–15, (1998).

O'Donnell–Maloney, Maryanne J. et al., Tibtech, 14, p. 401–407, (1996).

Fodor et al., Science, 251, p. 767–773, (1991).

Schober, A., et al., BioTechniques, 15(2), p. 324–329, (1993).

Czarnik et al., Modern Drug Discovery, 1(2), p. 49–55 (1998).

Kajiyama, T., et al, Micro Total Analysis Systems 2000, p. 505–508, (2000).

Corle, G.S., and Kino, G.S., Confocal Scanning Optical Microscopy and Related Imaging Systems, Chapter 1.3, Academic Press 1996.

Basarsky, T., Verdnik, D., Zhai, J.Y., & Wellis, D., Microarray Biochip Technology, p. 265–284, BioTechniques Books, edited by Mark Schena, Eaton Publishing (2000).

Brevnov, D., et al., Journal of Electroanalytical Chemistry 2000, 488(2), p. 133–139, (2000).

Senaratne, C; and Hanck, K.W., Chem. Instrumentation, 20(1), (1992).

Provance, J.D., Insulation/Circuits, p. 33–36, (1977).

Muskal, N., et al., Current Separations, 19(2), p. 49–54, (2000).-

ELECTRO-CHEMICAL ANALYSIS DEVICE WITH INTEGRATED THERMAL SENSOR AND METHOD FOR MONITORING A SAMPLE USING THE DEVICE

FIELD OF THE INVENTION

The present invention pertains to the analysis of biomolecular samples. More particularly, the present invention relates to fabrication and integration of thermal management techniques and devices for close proximity monitoring of a bioassay in a bioelectronic analyzer for the analysis of biomolecular samples such as nucleic acids.

BACKGROUND OF THE INVENTION

Molecular biology is an ever expanding field of study. Of great importance within the field of molecular biology is the detection and analysis of RNA, DNA, bacteria, proteins, and the like. Identification of molecular structure has become very important in many industries. In particular, biological molecules such as nucleic acids and proteins are analyzed to form the basis of clinical diagnostic assays. Currently it is predicted that a large market exits for bio-chips (micro-array chips) in the diagnosing and treating of diseases. Envisioned is a day when physicians will have the capabilities to use bio-chips to make an immediate genomic marker based diagnosis in their offices without the need for a lab as an intermediate diagnostic facility.

Currently, the greatest emphasis and market existence for bio-chips is within the field of genetic and pharmaceutical research, where many thousands of genes can be analyzed in parallel. The procedures utilized often involve large numbers of repetitive steps which consume large amounts of time. With the advent of large projects such as the human genome project, faster and less complex techniques are required.

Simpler and quicker analysis of molecules has been provided by the development of devices often referred to as biochips, which include arrays of test sites formed on a substrate platform. Each of the plurality of test sites includes probes therein to bond with target molecules from samples applied to the device. During analyzation, once certain conditions are met (discussed presently), the binding of a biomolecular to a probe is noted, thereby providing for the identification of the specific biomolecular.

DNA chips or microarrays generally consist of thin wafers of glass, silicon, plastic, printed circuit board (PCB), or ceramic having numerous microscopic bits of bio-molecules or porous support medium containing biomolecules, such as immobilized DNA probes sequences arrayed on the surface. These are used to identify specific disease genes and to speed drug discovery efforts. For example, microarray data has been used to identify gene clusters based on co-expression (Eisen, M. B. et al., Proc. Natl. Acad. Sci., 95, p. 14863–8, (1998)), define metrics that measure a gene's involvement in a particular cellular event or biochemical process (Spellman, P. T., et al., Molecular Biology of the Cell, 9, p. 3273–97, (1998)) and predict regulatory elements (Brazma, A., et al., Genome Research, 8, p. 1202–15, (1998)). It is anticipated that in the future increased use of bio-molecule related science will allow for a more personalized practice of medicine, more particularly the design and use of customized treatments and therapies based on a patient's genetic makeup (for review see Health Horizons articles on http://www.msnbc.com/news/horizons_front.html).

Currently, bio-chips, more specifically DNA chips, are known that are based on a common method of manufacture, namely the etching of silicon computer chips, as currently utilized in the semiconductor industry (O'Donnell-Maloney, Maryanne J. et al., Tibtech, 14, p. 401–407, (1996)). Of all of the uses of bio-chips to study bio-molecules, the study of DNA is the most mature. In one specific instance, a photoactivated DNA probe synthesis process is used to manufacture high density DNA chips (Fodor et al., Science, 251, p. 767–773, (1991)). Typically eighty photolithographic mask levels are used to synthesize DNA probes. Alternative approaches for dispensing reagents on a substrate have been reported in the prior art (e.g. U.S. Pat. No. 6,048,699, issued Apr. 11, 2000; U.S. Pat. No. 6,013,446, issued Nov. 1, 2000). In particular, the use of dispensing techniques to place purified, presynthesized oligonucleotides onto specific locations on a surface to produce a DNA chip is described in Schober, A., et al., BioTechniques, 15(2), p. 324–329, (1993) and U.S. Pat. No. 6,083,762, issued Jul. 4, 2000. The later technique does not require photolithography and requires fewer redundant probes because the purity of the probe sequences is much higher than in the photoactivated probe synthesis process. [E.P. 0910570 A1, issued Apr. 28, 1999; U.S. Pat. No. 6,312,960, issued Nov. 6, 2001].

An alternative means for synthesizing DNA probes is by using tiny micromirrors which allow for the placement of in excess of 300,000 bits of DNA onto a chip in just a few hours. In addition, the use of ink-jet printing is known, using high-speed robotic devices to print DNA on tiny squares of glass, to form an array. (U.S. Pat. No. 6,285,490B1, issued on Sep. 4, 2001). These types of machines are capable of forming as many as 32,000 DNA molecules on a single chip.

Still other methods include the use of fiber-optic bundles to build chips capable of holding 50,000 different DNA fragments on a single chip, and microelectronic chips that utilize electricity to attach DNA molecules to the surface of the chip. Other techniques can comprises the use of RF transponders, (U.S. Pat. No. 5,981,166A1, issued on Nov. 9, 1999), microbeads (Czarnik et al., Modern Drug Discovery, 1(2), p. 49–55 (1998)); U.S. Pat. No. 6,266,459B1, issued Jul. 24, 2001; U.S. Pat. No. 6,261,782B1, issued Jul. 17, 2001).

In the typical application, the biomolecular, or biological, sample that is being tested must be heated while held in the biochip to enhance kinetics prior to analyzation. In most instances, an external separate probe for temperature measurement is utilized to monitor the temperature of the biomolecular sample while the sample and biochip are placed in an oven or in conjunction with an external power source generating heating of the entire biochip or part thereof (e.g. the use of a Peltier heater/cooler requires mass transfer through at least the mass of the substrate of the chip on which said sample is attached that can typically limit the efficiency and duration of the thermal process to about 1 C/s). More particularly, the probe (e.g. resistance temperature device (RTD), pn junction, electrode, Kelvin probe, (e.g. used in atomic force microscopy) (AFM)) is in thermal contact with the biomolecular sample which must be heated to a given temperature and held at that temperature for a given period for analyzation of the sample to take place. Typically, a separate, externally located Peltier cooler/heater is utilized to accomplish this heating of the biomolecular sample and maintenance of the sample at the appropriate temperature. Prior to use, the heater must undergo calibration so that proper temperature sensing is achieved. (or alternative differential measurement). The bio-chip, containing the DNA probes and the biomolecular sample is introduced into a pre-calibrated oven chamber or preferably a calibrated Peltier heater, where the temperature is sensed and adjusted so that proper analyzation can take place. This presents not only an additional analyzation step, but a delay in a "sample in, data out" cycle. Furthermore, there is no control of the thermal profile at the chip level yielding to possible uncontrolled inhomogeneous thermal gradient at the sensor pad of the microarray of the biochip. More recently, Kajiyama et al. (Kajiyama, T., et al, Micro Total Analysis Systems 2000, p. 505–508, (2000) and E.P. No. 1108472A2, published on Jun. 20, 2001) described how to arrange DNA probes based on their melting temperature and hybridization using Si-islands that can be independently controlled by using the simple function of the pn-junction's voltage. Although, Kajiyama is teaching a method for attaching oligonucleotide probes to a silicon nitride surface, the method requires (i) chemically modifying the silicon nitride for generating reactive amino groups on the surface (ii) depositing probes at concentration greater than 25 $\mu$M and (iii) using dye-tagged PCR products for fluorescence scanning detection. Such an approach is costly, slow and not easily integratable. The present invention aims to overcome most of the limitations by combining highly sensitive and labeless bio-electronic detection of nucleic acid (e.g. single-stranded DNA) with high spatial thermal actuation and monitoring of a biochemical reaction. Continuous monitoring of a target binding process and quantitative measurements as well as the high degree of integration of such a platform are some of the critical improvements described in the present invention. The proposed apparatus doesn't require any washing steps that can interfere with in-situ thermal profiling as it has been published in the prior art.

Optical analysis of the biomolecular sample is typically utilized with conventional DNA chips. Many instances in the prior art require the binding of a fluorescent marker to the sample so that the amount of fluorescence of the marker bound to a diagnostic probe can be measured with an optical microscope system [Corle, G. S., and Kino, G. S., Confocal Scanning Optical Microscopy and Related Imaging Systems, Chapter 1.3, Academic Press 1996]. An optical system, such as a confocal-point microscope or an epifluorescence imaging microscope, may be utilized and the amount of the bonded sample is calculated on the basis of the amount of the fluorescence. Typically, the operation of most commercially available DNA chip scanners comprise an epifluorescence imaging microscope, a substantially planar wavelength-selective mirror holder disposed askew to a common optical pathway, the holder having a plurality of mirrors mounted thereon and having an axle attached normal thereto for rotating the holder so as to place a selected one of the mirrors in the common optical pathway. A motor is connected to the axle for rotating the mirror holder, either selectively or continuously. When a selected mirror is placed in the common optical pathway, the pathway is split so that an excitation light beam of one wavelength traveling along a source optical pathway from a light source is reflected by the mirror along the common optical pathway toward a sample (e.g. DNA spots of a microarray), while fluorescence light produced by the sample and directed back along the common optical pathway passes through the mirror to travel along a detector optical pathway to a detector (e.g. CCD camera). [Basarsky, T., Verdnik, D., Zhai, J. Y., & Wellis, D., Microarray Biochip Technology, p. 265–284, BioTechniques Books, edited by Mark Schena, Eaton Publishing (2000)]. Most of the fluorescence-based bioassay also require typically several labeling steps to incorporate some organic dye molecules within preferably a DNA sample. These steps are often costly, labor intensive and they can result in errors (e.g. loss of specificity due to unspecific binding).

It would be highly advantageous, therefore, to remedy the foregoing and other deficiencies inherent in the prior art. Accordingly, it is an object of the present invention to provide a new and improved apparatus for analyzing a biomolecular sample with integrated controlled thermal conditions, including a plurality of bio-molecules, and method for fabrication and use thereof.

Another object of the present invention is to provide a method and apparatus for analyzing bio-molecules in which an integrated biochip, including at least one integrated thermal sensor, is utilized to achieve on-chip direct temperature measurements and biosensing.

And another object of the present invention is to provide a method and apparatus for analyzing bio-molecules which is fast and efficient by controlling the environmental conditions (e.g. temperature, moisture, fluid mixing properties) of a sample in near proximity of a sensor array.

A further object of the present invention is to provide a method and apparatus for analyzing bio-molecules wherein the analyzing of the bio-molecules includes an integrated bio chip, including at least one thermal sensor, which is utilized to achieve on-chip direct temperature measurements and biosensing.

A further object of the present invention is to provide for a method and apparatus wherein biosensing is performed preferably by electronic detection of biological reactions such as nucleic acid hybridization (e.g. DNA, RNA) or protein interactions (e.g. immunoassay).

A still further object of the present invention is to provide for a method and apparatus for analyzing bio-molecules that provides for rapid deployment of an accurate analysis device with minimal manufacturing difficulty.

BRIEF DESCRIPTION OF THE DRAWINGS

The novel features believed characteristic of the invention are set forth in the claims. The invention itself, however, as well as other features and advantages thereof will be best understood by reference to detailed descriptions which follow, when read in conjunction with the accompanying drawings, wherein:

DETAILED DESCRIPTION OF THE PREFERRED EMBODIMENT

The above problems and others are substantially solved and the above purposes and others are realized in a chemical analysis device, such as a biomolecular analysis device, including a substrate platform, such as a printed circuit board (PCB) having integrated therein at least one thermal sensor, in close proximity with at least one biosensor and an energy source (e.g. resistive heater). The at least one thermal sensor and the at least one biosensor characterized as having a spatial resolution of less than 10 microns. In addition, included is a means for holding a sample, such as a bioreactor chamber, and associated electronics. The at least one thermal sensor is characterized as providing for the on-chip sensing of the temperature of a biomolecular sample held within the bioreactor chamber. At least one biosensor probe is integrated into the single platform and is characterized as including an electronically active electrode coated with at least specific DNA probes. A biomolecular sample is held in the bioreactor chamber and in thermal contact with the at least one biosensor probe. The at least one thermal sensor and the at least one biosensor are integrated and provide for the transferring of sensed temperature data into a measurement data set which could preferably allow for feedback control. Monitoring and control of the temperature of the biomolecular sample is achieved through a feedback circuit in electronic cooperation with the at least one thermal sensor and a means for heating the biomolecular sample.

Additionally disclosed is a method for monitoring a bioelectronic device, including the steps of providing at least one thermal sensor and at least one biosensor into an integrated platform. Provided is a means for holding the sample, such as a bioreactor chamber, positioned proximate with the at least one biosensor. During analyzation, the biomolecular sample is kept at a constant temperature by a means for heating the sample, such as an integrated resistive heater. The temperature of the biomolecular sample is sampled and monitored by the thermal sensor to produce an output measurement signal. The output measurement signal is interpreted by an external device which completes a feedback circuit, and submits a signal to the means for heating the sample, thereby providing for the maintenance of the biomolecular sample at a desired controlled (e.g. constant or with AC ramping) temperature during analyzation. Analyzation of the biomolecular sample is achieved at the biosensor sites based on electrical detection.

Figure 1:
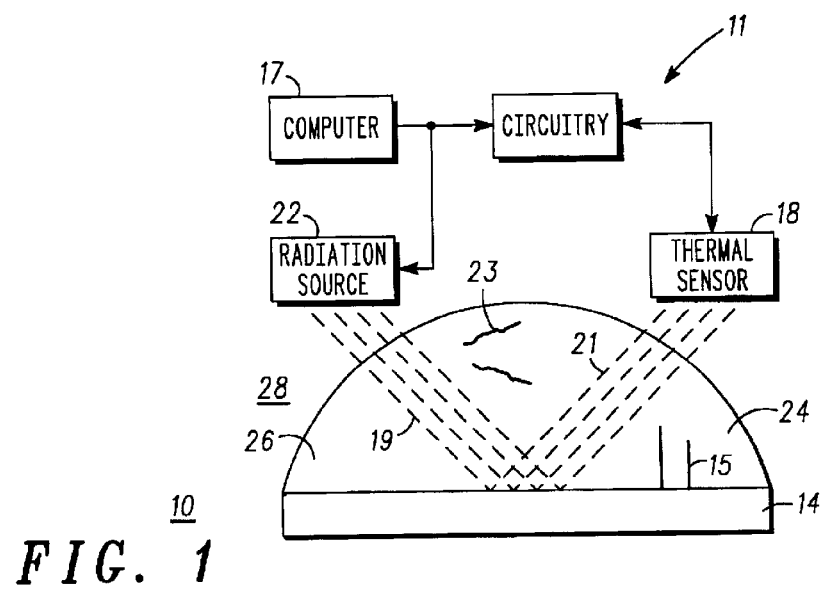
FIG. 1 is a simplified schematic view of a chemical analyzer according to the present invention.

During the course of this description, like numbers are used to identify like elements according to the different figures that illustrate the invention. Referring now to FIG. 1, illustrated in simplified schematic sectional view, is a chemical analyzer device 10 according to the present invention. Chemical analyzer device is generally comprised of at least one integrated biosensor 14, a thermal sensor 18, and a biomolecular sample 24. Biosensor 14 is typically formed of a gold electrode having a plurality of biomolecular probes 15 attached thereto. Biosensor 14 is formed proximate thermal sensor 18 and in thermal contact with sample 24. Biomolecular sample 24 in this particular example is illustrated as including a plurality of biomolecules 23, bound directly to a surface of biosensor 14 by physical interfacial surface tension and defining a first interface 26 and a second interface 28. Additionally, integrated is a means for heating sample 24, such as radiation source 22 which is sought to be analyzed.

Biochip 10 includes electronics 11, thereby placing thermal sensor 18 in electronic cooperation with an external monitoring device, such as a microprocessor 17, so as to achieve electronic detection and analyzation of sample 24. Biochip electronics 11 include a means for generating and transmitting an output signal, and receiving an input signal thereby providing for the maintenance of a preferred temperature for biomolecular sample 28. As illustrated in FIG. 1, an incident wave 19 is generated by radiation source 22 and is reflected by biosensor 14 toward thermal sensor 18 as either an equivalent wave, or as a signal wave 21, due to interaction at biosensor 14 that modulates incident wave 19, thus forming signaling wave 21. It is also anticipated by this disclosure to combine said sensor electrode operating as a thermal sensor and inversely said thermal probe operating as a nucleic acid sensor or biosensor (e.g. IR thermal sensor, CMOS imager operated as an electronic detector (i.e. electron transfer).

Figure 2:
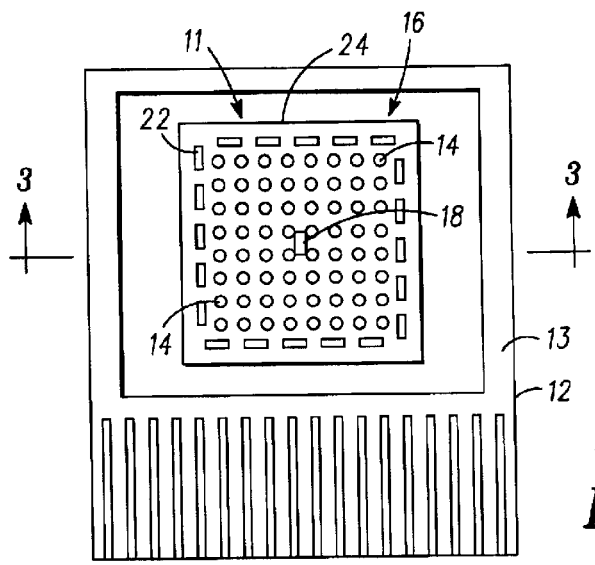
FIG. 2 is a simplified plan view of a chemical analyzer according to the present invention.
Figure 3:
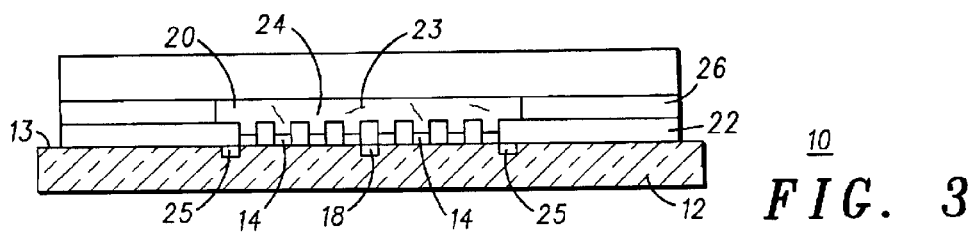
FIG. 3 is a simplified cross-sectional view taken along line 2—2 of FIG. 1, according to the present invention.

Referring now to FIGS. 2 and 3, illustrated is a simplified plan view of chemical analyzer device 10 according to the present invention and a simplified cross-sectional view of device 10 taken through line 3—3 of FIG. 2. Chemical analyzer device 10 is generally comprised of a substrate platform 12, the at least one integrated biosensor 14, the integrated thermal sensor 18 and a container for a fluid and or gas environment, and a means for holding biomolecular sample 24, such as a biomolecular sample. The means for holding sample 24 is described as generally comprised of structural means, such as a bioreactor chamber 20, but as previously described it could include any other means in which physical interfacial surface tension is at work, such as when sample 24 is provided as liquid that is bound directly to the surface of substrate platform 12, rather than by a structural means, such as bioreactor chamber 20. Additionally, integrated is the means for heating 22 sample 24 which is sought to be analyzed.

Device 10 is formed to include substrate platform 12. Substrate platform 12 generally serves as the support structure onto which the components of bioelectronic device 10 are formed. Substrate platform 12 is disclosed as being formed of any type of material that is biocompatible with sample 24 and reagents (e.g. enzymes), such as plastic, glass, printed circuit board (PCB), or the like. Substrate platform 12 has formed thereon an uppermost surface 13, the least one biosensor 14. In a preferred embodiment, substrate platform 12 has formed thereon uppermost surface 13 an array 16 of biosensors 14. Biosensors 14 are typically formed of a gold electrode having biomolecular probes attached thereto. Further information on biosensors such as that utilized as biosensor 14 can be found in U.S. Pat. No. 5,945,286 A1, entitled "METHOD FOR DETECTION OF POLYNUCLEOTIDE HYBRIDIZATION", issued on Aug. 31, 1999; U.S. Pat. No. 6,290,839 entitled "SYSTEMS FOR ELECTROPHORETIC TRANSPORT AND DETECTION OF ANALYTES", issued on Sep. 18, 2001; and U.S. Pat. No. 6,264,825, entitled "BINDING ACCELERATION TECHNIQUES FOR THE DETECTION OF ANALYTES", issued on Jul. 24, 2001, all of the above being incorporated herein by this reference.

More specifically, each biosensor 14 is disclosed as formed of an electronically active electrode coated with a specific DNA probe. The term "probe" as used herein, is intended to describe substances which can specifically detect a particular substance, site, state and the like. The term includes oligonucleotide DNA/RNA probes, protein probes such as antibodies, and the like. In the instance of an oligonucleotide probe, either single strand or double strand is intended.

Biosensors 14 operate on the basis of bioelectronics in which electronic circuits or equivalent are coupled to biological molecules (preferably redox reactions for ACV measurement). Preferably, the electronic DNA sensor chip consists of an array of gold electrodes modified with a multi-component SAM that includes pre-synthesized capture probes that are covalently attached to the electrode through an alkyl thiol linker. SAM incorporating probes of different sequences can be formed on the surface of each addressable working electrode pad. An hybridization chamber is assembled with the array to form a three electrode electrochemical system into which labeled targets (e.g. ferrocene) can be introduced. Measurements are then performed in situ using alternating current voltammetry or ACV [U.S. Pat. No. 6,277,576B, entitled "NUCLEIC ACID MEDIATED ELECTRON TRANSFER", issued Aug. 21, 2001; Brevnov, D., et al., Journal of Electroanalytical Chemistry 2000, 488(2), p. 133–139, (2000); Senaratne, C; and Hanck, K. W., Chem. Instrumentation, 20(1), (1992).

During operation, target biomolecules, preferably in the form of a biofluid, such as DNA found in blood, plant, or food, for instance, alter the electronic circuit at the electrode surface. The change can be readily sensed by electronics 11, and more particularly an electronic instrument, as a positive indication of the target biomolecules presence or a negative indicator of the lack of presence of target biomolecules such as through depletion or quenching. Biosensors 14 as disclosed herein, do not operate on the basis of optical detection, typically achieved through the use of fluorescent markers. Biosensors 14, including probes 15, formed on the chips surface "capture" specific target DNA present in the sample. The capture event generates a unique and characteristic electrical signal. Further information on the biosensors, or bioprobes, formed according to this manner can be found in the following U.S. patent references: (i) U.S. Pat. No. 6,063,573, entitled "CYCLING PROBE TECHNOLOGY USING ELECTRON TRANSFER DETECTION", issued May 16, 2000; (ii) U.S. Pat. No. 6,071,699, entitled "NUCLEIC ACID MEDIATED ELECTRON TRANSFER", issued Jun. 6, 2000; (iii) U.S. Pat. No. 6,087,100, entitled "NUCLEIC ACID MEDIATED ELECTRON TRANSFER", issued Jul. 11, 2000; (iv) U.S. Pat. No. 6,090,933, entitled "METHODS OF ATTACHING CONDUCTIVE OLIGOMERS TO ELECTRODES", issued Jul. 18, 2000; (v) U.S. Pat. No. 6,096,273, entitled "ELECTRODES LINKED VIA CONDUCTIVE OLIGOMERS TO NUCLEIC ACIDS", issued Aug. 1, 2000; (vi) U.S. Pat. No. 6,013,170, entitled "DETECTION OF ANALYTES USING REORGANIZATION ENERGY", issued Jan. 11, 2000; and (vii) U.S. Pat. No. 6,013,459, entitled "DETECTION OF ANALYTES USING REORGANIZATION ENERGY, issued Jan. 11, 2000. All of the above being incorporated herein by this reference.

Biosensor array 16 has formed in contact therewith, a means for holding sample 24, such as bioreactor chamber 20. Bioreactor chamber 20 is formed preferably integral with substrate platform 12 and characterized as providing for a chamber to hold biomolecular sample 24 during analysis. Bioreactor chamber 28 in a preferred embodiment is defined by a seal 26 as illustrated in FIG. 2. Seal 26 is generally formed of some "biocompatible" material, such as adhesive Mylar®, silicone based tape, or the like and serves to define chamber 20. Chamber 20 defines a holding area into which a biomolecular sample 24 is placed for analyzation. Chamber 20 is formed to provide for physical contact between biosensors 14 and biomolecular sample 24. For example, chamber 20 is compatible to perform a biomolecular amplification reaction such as a polymerized chain reaction. It is anticipated herein, that in lieu of bioreactor chamber 28, sample 24 can be held in place on substrate platform 12 by interfacial surface tension. In this instance, an actual "structure" such as bioreactor chamber 20 would not be necessary.

As previously stated, integrated thermal sensor 18 is formed in thermal contact with bioreactor chamber 20 and biomolecular sample 24. More specifically, thermal sensor 18 is disclosed as formed having a spatial resolution of less than 10 microns (<10 $\mu$m) between thermal sensor 18, fluid containers and biosensors 16. Thermal sensor 18 is characterized as providing for the sensing of a temperature of biomolecular sample 24 and providing sensed temperature data. Thermal sensor 18 is designed to provide for the reading and monitoring of the temperature of biomolecular sample 24 during analyzation with a preferred temporal resolution of less than 10 milliseconds (<10 ms) and being accurate to within less than 0.1 degree centigrade (<0.1° C.). Thermal sensor 18 is formed integral with substrate platform 12 either positioned on a surface of substrate platform 12 or embedded three-dimensionally within substrate platform 12 as illustrated in FIG. 3. Thermal sensor 18 serves to monitor the temperature of biomolecular sample 24 during the analyzation process.

Thermal sensor 18 is described in this preferred embodiment as comprised of a p-n junction, such as a thermal semiconductor diode, which operates by detecting a change in temperature as a function of the pn junction voltage. Alternatively, thermal sensor 18 is disclosed as comprised of a thermistor, a resistance temperature detector (RTD), or other types of thermal sensors well known in the art.

Figure 4:
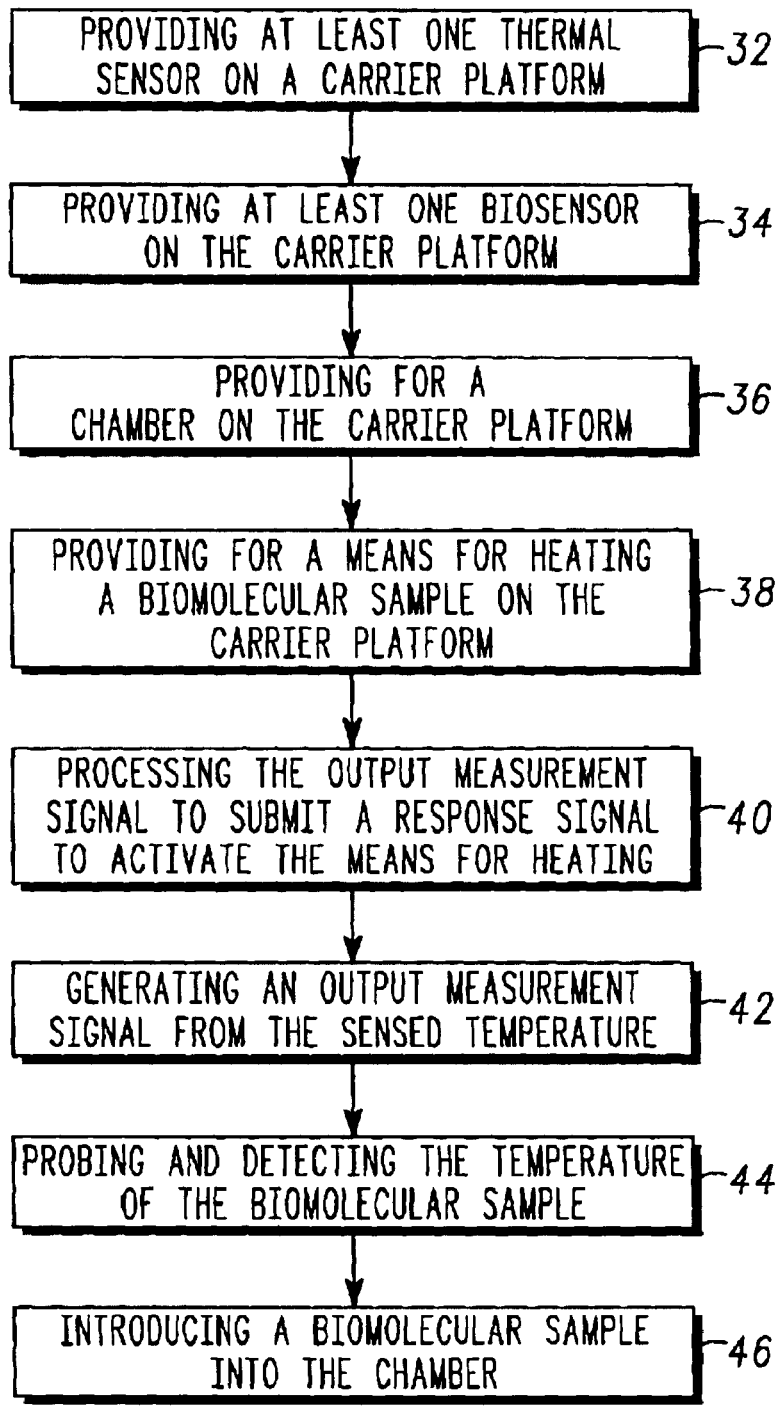
FIG. 4 is a simplified flow chart illustrating a method for monitoring a biomolecular sample using a biomolecular analysis device according to the present invention.

Referring now to FIG. 4, as previously described, during the analyzation process 30, biomolecular sample 24 must be kept at a constant preferred temperature for hybridization, or attachment of a specific molecule to the biosensor probe 14. Initially, in the process provided is the three-dimensional integration on a single substrate platform of the at least one thermal sensor 18, the at least one biosensor 14, and the bioreactor chamber 24, steps 32, 34 and 36, respectively. To achieve a constant desired temperature, the means for providing heat 22 is formed 38 integral with substrate platform 12 and proximate biosensors 14, thermal sensor 18 and biomolecular sample 24. The means for providing heat 22 is disclosed as being accurate to within less than 0.1 degree centigrade (<0.1° C.). As disclosed in this preferred embodiment, providing heat to biomolecular sample 24 takes place utilizing a resistive film 25, as illustrated in FIG. 2. In this particular embodiment, resistive film 25 is formed to completely encompass array of biosensors 16 being formed as resistive stripes. Other means of forming the resistive layer, such as a planar resistive film layer embedded in substrate platform 12 are anticipated by this disclosure. Resistive film 25, as illustrated in FIG. 3, is embedded in substrate platform 12 and thus provides for radiant heating of the biomolecular sample 24 through substrate platform 12. Resistive film 25 is electronically configured to receive an input signal from an external driver that is formed as a feedback circuit with thermal sensor 18. This input signal forces the means for heating 22 to a desired value thus enabling the preservation of a desired temperature for biomolecular sample 24. This inclusion of resistive film 25 provides for the maintenance of biomolecular sample 24 at a constant temperature during the analyzation process, thus allowing for hybridization (e.g. DNA hybridization, single stand DNA, double strand DNA/RNA, protein reaction) to take place.

In an alternative embodiment, the means for heating 22 biomolecular sample 24 is disclosed as including a heating source based on one of a fluidic heat source, a chemical reaction, magnetic induction, microwave RF, air convection, or the like. It is understood that the means for heating 22 provides for even heating of biomolecular sample 24. In the preferred embodiment and for the sake of integration, a resistive heating element is embedded into the bioelectronic sensor array platform. Temperature control elements (e.g. pn junctions) are also integrated within the platform to control the temperature. The invention provides heating elements, specifically resistive heating elements, and elements for detecting temperature at specific spatial positions on the platform. Heating devices are preferably arrayed to control the temperature of the platform over a particular and defined area, and are provided having a steep temperature gradient with distance on the platform from the heater (e.g. >1 micron). Certain resistors, including commercially-available resistive inks (available from Dupont®) exhibit a positive temperature coefficient (PTC), i.e., an increase in resistance with increasing temperature. Applying a fixed voltage across a PTC resistor screen-printed on a plastic substrate results in rapid heating, followed by self-regulation at an elevated temperature defined by the circuit design heat sink and ambient temperature. In such screen-printed resistors, connection to a power source is made by first printing parallel silver conductors followed by printing the PTC ink between the conductors. Typically, a resistive heating element comprises a conductive ink connected with electrical contacts for activation of the heater and resistive inks applied between the conductive ink and in electrical contact therewith, wherein application of a voltage (direct or alternating current) between the conductive inks results in current a voltage (direct or alternating current) between the conductive inks results in current flow through the resistive inks and production of heat. There are two types of resistive inks for the resistive heating elements. The first can be a standard polymer thick film ink, such as Dupont® 7082 or Dupont® 7102 ink. These inks produce a surface temperature that is not self-limiting, and the temperature resulting from the use of these inks is dependent primarily on the magnitude of the applied voltage. In contrast, the positive temperature coefficient (PTC) inks show increased resistivity with increasing voltage, so that surface temperature is self-limiting because the amount of heat-producing current goes down as the applied voltage goes up. PTC inks are characterized as having a particular temperature where this self-limiting property is first exhibited; at voltages that produce temperatures less than the critical temperature, the amount of heat is dependent on the magnitude of the applied voltage.

Resistive inks useful according to the invention include any commercially available polymer thick film ink and PTC inks (e.g. Dupont® 7082, 7102, 7271, 7278 and 7285, and other equivalent). Conductive inks can include commercially available conductive inks (e.g. Dupont® 5028, 5025, and other equivalent). Additional dielectric layers advantageously comprise dielectric inks such as Dupont® 5018A. Insulation can also be achieved using pressure sensitive transfer adhesive such as 7952 MP (3M®), or a pressure sensitive transfer adhesive deposited onto a polyester carrier layer such as 7953 MP (3M®) or thermoplastic bonding films such as 406, 560 or 615 (3M®). Resistive heaters can be used to incubate fluids at a stable temperature or also for thermal cycling (e.g. useful when integrating an amplification PCR chamber with the bioelectronic detection platform).

Resistive and conductive inks are preferably screen-printed using methods and techniques well known in the art. See Provance, J. D., Insulation/Circuits, p. 33–36, (1977). Inks are typically screen printed to a thickness of about 10 microns; however, repetitive screen printing of resistive inks can be used to deposit thicker layers at between 110° C. and 120° C. for about 10 minutes. Heaters can be screen printed to any required size; a minimum area for a screen-printed heater has been determined to be about 0.25 mm$^2$ (0.5 mm×0.5 mm) to produce useful energy for a bioassay. The choice of ink formulation, multiplayer printing and the type of connections (e.g. series or parallel) can allow for customized thermal properties.

There are several thermal measurement techniques (i.e. contact and non contact methods) compatible with the present invention such as the use of thermocouple probes (e.g. thin film single crystal ceramic garnet), optical temperature measurement (e.g. higher frequency temperature fluctuations which may also occur in an embodiment where a fluid is moved into the apparatus chamber), thermal lens techniques [Harris J. M., in Analytical Applications of Laser, edited by E. H. Piepmeier, Wiley, New York, N.Y., Chap. 3, pp. 1–476, 1986] and preferably thermal diode measurement. A general concept comprises the use of integrated temperature sensors made in standard CMOS technology [U.S. Pat. No. 6,080,969 A1, entitled "APPARATUS FOR AND METHOD OF THERMALLY PROCESSING SUBSTRATE, issued Jun. 27, 2000; U.S. Pat. No. 6,230,497 B1, entitled "SEMICONDUCTOR CIRCUIT TEMPERATURE MONITORING AND CONTROLLING APPARATUS AND METHOD", issued May 15, 2001]. Most of the semiconductor devices exploit a voltage drop across a forward biased pn junction in silicon which depends on temperature with a gradient (e.g. about −2 mV/K). A typical temperature coefficient is used for on substrate temperature measurement which the substrate (e.g. PCB board with gold pads array) temperature is determined. Note that pn junctions can be found in vertical bipolar devices in conventional CMOS technologies.

Additionally, integrated into substrate platform 12 is a reference probe 28 formed proximate biosensor 16 and integral substrate platform 12. Reference probe 28 is characterized as performing as an electro-chemical reference for biosensors 14. Typically a Ag/AgCl reference electrode is used in the proposed bioelectronic device. A preferred embodiment uses AC Voltammetry and its modifications, specifically, fourth Harmonic AC Voltammetry (i.e. non linear component of the electrochemical response). Such electrochemical method is mainly used to characterize the rates of faradaic reactions (heterogeneous electron transfer) between either soluble or adsorbed redox couples and gold electrodes of biosensor 14 across thin organic films such as hybrid bilayer membranes and self-assembled monolayers. Typical 100 Hz, fourth harmonic ACV is measured generating a symmetrical four-peak shape signal of a positive scan (when scanning an oxidation/reduction cycle) centered about 180 mV which represents the oxidation potential of a ferrocene label. Then signal analysis algorithms are used to identify and quantify the positive and negative signal peaks. In practice, duplicate pads with similar DNA sequences are averaged for better S/N. However, any electrochemical method known in the prior art is also appropriate within the scope of the present invention [Muskal, N., et al., Current Separations, 19(2), p. 49–54, (2000)].

During operation 30, biochip 10, including the three-dimensionally integrated structures, is filled with biomolecular sample 24, step 40. In an alternative embodiment, sample 24 is simply placed in contact with substrate platform 12 surface. Biochip 10 is placed in an external reader (not shown), having included as parts thereof, electronics to complete the feedback circuit. Thermal sensor 18 determines 42 the temperature of the biomolecular sample 24 and submits an output signal 44 to the reader, which in turn returns a signal 46 to means for heating 22 to adjust the temperature, thereby heating biomolecular sample 24 and allowing for hybridization to take place. Such signal transmission between emitter and receiver could comprise wireless transmission, remoteless or internet based communication protocols It is disclosed that once hybridization takes place, the change in electric condition (e.g. voltage, current and/or power) is recorded and identification of the molecule within biomolecular sample 24 is made by utilizing the exterior reader. Accordingly, included are electronics for the transforming the sensed temperature data into an output measurement signal, the electronics operate by way of a feedback circuit between the means for providing heat 22 and thermal sensor 18, thereby providing for the maintenance of a preferred temperature for the biomolecular sample 24.

Accordingly, disclosed is a device and method for analyzing biomolecular samples. The device includes a plurality of integrated structures formed within specific tolerances, thereby forming a compact biochip package having a volume resolution of less than 50 microliters (<50 μL). The device as described provides for the inclusion of a thermal sensor for determining the temperature of the biomolecular sample and a means for heating the biomolecular sample, so as to provide a controlled (e.g. constant) temperature for hybridization to occur, thus allowing for biomolecular analyzation. The inclusion of the integrated thermal sensor, integrated heater and integrated bioarray of biosensors provides for a single chip in which calibration and use of an external heating device is not required. Thus, disclosed is a compact integrated biochip for use in analyzing biomolecular samples thus allowing for the simultaneous sensing of a plurality of bioassay in less than approximately 4 hours.

While we have shown and described specific embodiments of the present invention, further modifications and improvement will occur to those skilled in the art. We desire it to be understood, therefore, that this invention is not limited to the particular forms shown and we intend in the appended claims to cover all modifications that do not depart from the spirit and scope of this invention.

What is claimed is:

1. An electro-chemical analysis device, comprising:
   a means for holding a sample undergoing analyzation;
   at least one thermal sensor for sensing the temperature of the sample during analyzation and providing sensed temperature data;
   at least one biosensor, formed proximate the thermal sensor and in thermal contact with the sample, comprising an array of biological probes each of the biological probes characterized as including an electronically active electrode coated with a specific DNA probe;
   a means for providing radiation to the sample, wherein the at least one thermal sensor, the at least one biosensor, and the means for providing heat are three-dimensionally integrated in a single substrate platform;
   electronics for transforming the sensed temperature data into an output measurement signal, the electronics formed as part of a feedback circuit, thereby providing for the maintenance of a preferred temperature of the sample.

2. An electro-chemical analysis device as claimed in claim 1 wherein the at least one thermal sensor and the at least one biosensor are formed having a spatial resolution of less than 10 microns.

3. An electro-chemical analysis device as claimed in claim 2 wherein the at least one thermal sensor has a temporal resolution of less than 10 milliseconds.

4. An electro-chemical analysis device as claimed in claim 3 wherein the electro-chemical analysis device has a volume resolution of less than 50 microliters.

5. An electro-chemical analysis device as claimed in claim 4 wherein the means for holding a sample undergoing analyzation is a bioreactor chamber.

6. An electro-chemical analysis device as claimed in claim 4 wherein the means for holding a sample undergoing analyzation is interfacial surface tension.

7. An electro-chemical analysis device as claimed in claim 4 wherein the sample is a biomolecular sample.

8. A biomolecular sample as claimed in claim 7 wherein the sample is a nucleic acid biomolecule, DNA, RNA or a protein.

9. An electro-chemical analysis device as claimed in claim 4 wherein the at least one thermal sensor is formed as one of a p-n junction, a thermistor, or a resistance temperature detector (RTD).

10. An electro-chemical analysis device as claimed in claim 4 wherein the means for providing radiation to the biomolecular sample includes generating radiant heat by one of a thermal reaction, a chemical reaction, a fluid, or magnetic induction, proximate the biomolecular sample to heat the sample.

11. An electro-chemical analysis device, comprising:
    a substrate platform;
    a bioreactor chamber formed integral with the substrate platform, the bioreactor chamber characterized as providing for a chamber to hold a biomolecular sample during analysis;
    at least one thermal sensor formed in thermal contact with the bioreactor chamber and the biomolecular sample and integral with the substrate platform, the at least one thermal sensor characterized as providing for the sensing of a temperature of the biomolecular sample and having a temporal resolution of less than 10 milliseconds, the at least one thermal sensor providing sensed temperature data and having a temperature resolution of less than 0.1 degree centigrade;
    a plurality of biosensors, formed having a spatial resolution of less than ten microns to the at least one thermal sensor, wherein the plurality of biosensors are formed integral with the substrate platform and in physical contact with the biomolecular sample, wherein each said biosensor includes an electronically active electrode coated with a specific DNA probe;
    a reference probe formed proximate the at least one biosensor and integral the substrate platform, the reference probe characterized as performing as an electrochemical reference;
    a means for providing radiation to the biomolecular sample formed integral with the substrate platform, and in thermal contact with the biomolecular sample; and
    a means for the transforming the sensed temperature data into an output measurement electrical signal, the means for transforming the sensed temperature data formed as part of a feedback circuit with the means for providing heat to the biomolecular sample, thereby providing for the maintenance of a preferred temperature for the biomolecular sample.

12. An electro-chemical analysis device as claimed in claim 11 wherein the at least one thermal sensor is formed as one of a p-n junction, a thermistor, or a resistance temperature detector (RTD).

13. An electro-chemical analysis device as claimed in claim 11 wherein the means for providing radiation to the biomolecular sample includes providing radiant heat, generated by a resistive film formed proximate the bioreactor chamber.

14. An electro-chemical analysis device as claimed in claim 11 wherein the means for providing radiation to the biomolecular sample includes providing for a chemical reaction proximate the bioreactor chamber, the chemical reaction generating radiant heat to heat the biomolecular sample.

15. An electro-chemical analysis device as claimed in claim 11 wherein the means for providing radiation to the biomolecular sample includes providing for magnetic induction of heat proximate the biocompatible to heat the biomolecular sample.

16. A method for monitoring a sample using an electro-chemical analysis device, comprising the steps of:
provOiding at least one thermal sensor having a temporal resolution of less than 10 milliseconds and at least one biosensor three-dimensionally related on a substrate platform, the at least one thermal sensor and the at least one biosensor positioned having a spatial resolution of less than 10 microns, wherein the at least one biosensor includes an electronically active electrode coated with a specific DNA probe,
providing for a bioreactor chamber integrated with the substrate platform, and formed proximate the at least one biosensor, the bioreactor chamber characterized as holding a biomolecular sample for testing;
providing a means for providing radiation to the biomolecular sample formed integral the substrate platform;
introducing a biomolecular sample into the bioreactor chamber, the biomolecular sample characterized as being in thermal contact with the at least one thermal sensor and in physical contact with the at least one biosensor, the biomolecular sample having a temperature;
probing and detecting the temperature of the biomolecular sample with the thermal sensor;
generating an output measurement electrical signal from the sensed temperature;
processing the output measurement signal to submit a response signal to activate the means for providing radiation.

17. A method for monitoring a biomolecular sample using an electro-chemical analysis device as claimed in claim 16 wherein the step of providing at least one thermal sensor includes providing one of a p-n junction, a thermistor, or a resistor temperature detector (RTD).

18. A method for monitoring a biomolecular sample using an electro-chemical analysis device as claimed in claim 16 wherein the step of providing a means for providing radiation to the biomolecular sample includes providing radiant heat generated by one of a resistive film formed proximate the bioreactor chamber, a chemical reaction proximate the bioreactor chamber, or magnetic induction of heat proximate the bioreactor chamber to heat the biomolecular sample.

* * * * *

UNITED STATES PATENT AND TRADEMARK OFFICE
CERTIFICATE OF CORRECTION

PATENT NO. : 6,756,223 B2
DATED : June 29, 2004
INVENTOR(S) : Peter C. Roberts et al.

It is certified that error appears in the above-identified patent and that said Letters Patent is hereby corrected as shown below:

<u>Column 13</u>,
Line 14, insert the following after "includes", -- a plurality of biological probes, each of the plurality of biological probes are characterized as including --.

Signed and Sealed this

Fourteenth Day of December, 2004

JON W. DUDAS
*Director of the United States Patent and Trademark Office*